(12) United States Patent
Szalay et al.

(10) Patent No.: US 6,984,374 B2
(45) Date of Patent: Jan. 10, 2006

(54) METHOD FOR THE EVALUATION OF IMPLANTABLE MATERIALS

(75) Inventors: Aladar A. Szalay, Highland, CA (US); Shahrokh Shabahang, Redlands, CA (US); Yong Yu, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 10/356,245

(22) Filed: Jan. 30, 2003

(65) Prior Publication Data

US 2003/0133949 A1 Jul. 17, 2003

Related U.S. Application Data

(62) Division of application No. 09/769,981, filed on Jan. 25, 2001.

(60) Provisional application No. 60/178,538, filed on Jan. 26, 2000.

(51) Int. Cl.
*A61K 49/00* (2006.01)
*A61B 5/055* (2006.01)
*A61B 10/00* (2006.01)
*A61B 5/00* (2006.01)
*A61B 8/00* (2006.01)

(52) U.S. Cl. .............. 424/9.1; 424/9.341; 424/9.351; 424/9.6; 435/4; 435/7.2; 435/7.32; 435/7.95; 435/29; 435/31; 435/32; 435/34; 435/173.1; 435/243; 435/320.1; 436/164; 436/171; 436/172

(58) Field of Classification Search ............... 424/9.1, 424/9.341, 9.351, 9.6; 435/4, 7.2, 7.32, 7.95, 435/29, 31, 32, 34, 173.1, 243, 320.1; 436/164, 436/171, 172
See application file for complete search history.

(56) References Cited

U.S. PATENT DOCUMENTS

| 4,036,698 A | 7/1977 | Bush et al. .......... 195/103.5 M |
| 5,422,240 A | 6/1995 | Lytle et al. .................... 435/5 |
| 5,736,351 A * | 4/1998 | Miller et al. .................... 435/8 |
| 5,814,331 A | 9/1998 | Holen ........................ 424/435 |

FOREIGN PATENT DOCUMENTS

EP 0045137 A2 6/1981

OTHER PUBLICATIONS

Billard, P. et al., "Bioluminescence-based assays for detection and characterization of bacteria and chemicals in clinical laboratories," *Clin. Biochem.*, Abstract, 31(1):1-14 (Feb. 1998).

Contag, C.H. et al., "Photonic detection of bacterial pathogens in living hosts," *Mol. Microbiol.*, Abstract, 18(4): 593-603 (Nov. 1995).

Francis, K.P. et al., "Monitoring bioluminescent *Staphylococcus aureus* infections in living mice using a novel luxABCDE construct," *Infect. Immun.*, Abstract, 68 (6):3594-600 (Jun. 2000).

(Continued)

*Primary Examiner*—Lynette R. F. Smith
*Assistant Examiner*—J. Hines
(74) *Attorney, Agent, or Firm*—David A. Farah; Sheldon & Mak PC

(57) ABSTRACT

A method for the evaluation of a material to determine whether the material is susceptible to bacterial contamination or colonization comprising providing bacteria which are modified to produce a first detectable signal, exposing the material being evaluated to the bacteria and determining whether the first signal is present determining whether the first signal is present on the material or within the material.

10 Claims, 2 Drawing Sheets

OTHER PUBLICATIONS

Hoffman, A. et al., "Fate of plasmid-bearing, luciferase marker gene tagged bacteria after feeding to the soil microarthropod *Onychiurus fimatus* (Collembola)," *FEMS Microbiol. Ecol.*, Abstract, 30(2):125-135 (Oct. 1999).

Kurittu, J. et al., "A group-specific microbiological test for the detection of tetracycline residues in raw milk," *J. Agric. Food Chem.*, Abstract, 48(8):3372-7 (Aug. 2000).

Kurittu, J. et al., "Detection of tetracyclines with luminescent bacterial strains," *Luminescense*, Abstract, 15 (5):291-7 (Sep. 2000).

Lee, S.H. et al., "Novel approaches to monitor bacterial gene expression in infected tissue and host," *Curr. Opin. Microbiol.*, Abstract, 3(1):97-101 (Feb. 2000).

Loessner, M.J., "Evaluation of luciferase reporter bacteriophage A511; luxAB for detection of *Listeria monocytegenes* in contaminated foods," *Appl. Environ Microbiol.*, Abstract, 63(8):2962-5 (Aug. 1997).

Prosser, J.I. et al., "Luminescense-based systems for detection of bacteria in the environment," *Crit. Rev. Biotechnol.*, Abstract, 16(2):157-83, (1996).

Siragusa, G.R. et al., "Real-time monitoring of *Escherichia coli* 0157:H7 adherence to beef carcass surface tissues with a bioluminescent reporter," *Appl. Environ. Microbiol.*, Abstract, 65(4):1738-45 (Apr. 1999).

Voisey, Christine R. et al., "Elimination of Internal Restriction Enzyme Sites from a Bacterial Luminescense (luxCDABE) Operon," *Biotechniques*, 24(56):58 (Jan. 1998).

Patrick Billard and Michael S. Dubow, *Bioluminescence-Based Assays for Detection and Characterization of Bacteria and Chemicals in Clinical Laboratories*, Clinical Biochemistry, vol. 31, Feb. 1998, pp. 1-14.

G.D. Behrend, C.W. Cutler and J.L. Gutmann, *An in-vitro study of smear layer removal and microbial leakage along root-canal filings*, International Endodontic Journal (1996) 29, 99-107.

Giano Ricci, Giulio Rasperini, Maurizio Silvestri and Pier Sandro Cocconcelli, *In Vitro Permeability Evaluation and Colonization of Membranes for Periodontal Regeneration by Porphyromonas gingivalis*, J Periodontal May 1996 pp. 490-496, XP008014695.

L.B. Peters, P.R. Wesselink and W.R. Moorer, *Penetration of bacteria in bovine root dentine in vitro*, International Endodontic journal, 33, 28-36, 2000, XP-002234215.

Contag et al., "Photonic Detection of Bacterial Pathogens in Living Hosts," 1995, Mat. Micro. 18(4): 593-603.

Loessner et al., "Evaluation of Luciferase Reporter Bacteriophage A511:JuxAB for Detection of *Listeria monocytogenes* in Contaminated Foods," 1997, Applied and Environ. Microb. 63(8):2961-2965.

* cited by examiner

METHOD FOR THE EVALUATION OF IMPLANTABLE MATERIALS

CROSS-REFERENCE TO RELATED APPLICATION

This application is a divisional application of U.S. patent application Ser. No. 09/769,981, entitled "Method For The Evaluation of Implantable Materials," filed Jan. 25, 2001 which claims the benefit of U.S. Patent Application 60/178,538, entitled "Method For The Evaluation of The Sealing Ability of Dental Products," filed Jan. 26, 2000; and the present application claims the benefit of PCT patent application PCT/US01/02515, entitled "Method For The Evaluation of Implantable Materials," filed Jan. 25, 2001, the contents of which are incorporated by reference herein in their entirety.

BACKGROUND

A wide variety of natural and artificial materials are implanted in humans and animals during the treatment of injuries, conditions and diseases. Among the common uses for these materials are as sutures and as filling material for dental cavities.

A variety of methods are currently used to determine whether materials can prevent bacterial contamination from passing through or around the material. In one method, materials intended to fill cavities in teeth are tested by cleaning out the canals of a natural extracted tooth, sealing the root end of the tooth with the material being tested and filling the center with a test substance. The test substance can be a radioisotope, a dye or bacteria. The sealed tooth is then placed in a container with the sealed end contacting a test medium. Over time, the test medium is checked for presence of the test substance to determine whether the material has effectively prevented the test substance from leaking out of the center of the tooth.

Though useful, this method has several disadvantages. Radioisotopes are difficult to work with and are potentially dangerous. The presence of dye in the test medium does not necessarily indicate that bacteria would breech the test material because dyes have a much smaller molecular size than bacteria. Finally, the presence of bacteria in the test medium can indicate that the testing apparatus itself was contaminated rather than that the material was breeched.

Additionally, wound closure materials are currently tested by looking at the amount of inflamation the material causes in vivo. However, there is no current method for determining whether wound closure material is subject to bacterial contamination or colonization.

Therefore, it would be useful to have a method of testing materials to determine whether they are subject to bacterial contamination or colonization. Further, it would be useful to have another method of testing whether materials can prevent bacteria from passing through or around the material.

SUMMARY

According to one embodiment, the present invention is a method for evaluating whether a material will allow bacteria to pass through the material or pass into the material. The method comprises, first, providing bacteria which are modified to produce a first detectable signal. Then, the bacteria are placed on a first side of the material being evaluated, and a determination is made whether the first signal is present on a second side of the material or within the material. Absence of the first signal on the second side of the material or within the material indicates that the bacteria have not passed through or around the material. Presence of the first signal on the second side of the material or within the material indicates that the bacteria have passed through or around the material.

In a preferred embodiment, the method additionally comprises quantifying the amount of bacteria that will pass through the material or into the material by quantifying the amount of the first signal on the second side of the material. Increasing amounts of the first signal on the second side of the material or within the material indicates increasing amounts of bacteria that will pass through, around or into the material.

In another preferred embodiment, the bacteria are modified to produce a second detectable signal, and the method additionally comprises determining whether the second signal is present on the second side of the material or within the material. Absence of the second signal on the second side of the material or within the material indicates that the bacteria have not passed through or around the material or into the material. Presence of the second signal on the second side of the material or within the material indicates that the bacteria have passed through, around or into the material.

In a preferred embodiment, the first signal is light emission in the visible spectrum. In another preferred embodiment, the second signal is light emission in the visible spectrum. In a particularly preferred embodiment, there the bacteria are modified to incorporate a functional green fluorescent protein. In another particularly preferred embodiment, the bacteria are modified to incorporate a functional luciferase. In yet another particularly preferred embodiment, the bacteria are modified to incorporate both a functional green fluorescent protein and a functional luciferase.

In one embodiment of the present invention, placing the bacteria on a first side of the material being evaluated comprises placing the bacteria in the center of a hollowed out, extracted natural tooth where the root end of the tooth is sealed with the material, and then placing the root end of the tooth in a test medium. Then, a determination is made whether the first signal is present on a second side of the material or within the material by detecting the first signal in the test medium or within the material. In a particularly preferred embodiment, the bacteria provided are additionally modified to be grown selectively, such as due to antibiotic resistance.

According to another embodiment of the present invention, there is provided a method for the evaluation of a material to determine whether the material is susceptible to bacterial contamination or colonization when implanted into an animal or human. The method comprises providing bacteria which are modified to produce a first detectable signal. Next, the material being evaluated is exposed to the bacteria. Then, a determination is made whether the first signal is present on the material or within the material. Absence of the first signal on the material or within the material indicates that the material is not susceptible to bacterial contamination or colonization. Presence of the first signal on the material or within the material indicates that the material is susceptible to bacterial contamination or colonization.

In a preferred embodiment, the method additionally comprises quantifying the susceptibility of the material to bacterial contamination or colonization by quantifying the amount of the first signal on the material or within the material. Increasing amounts of the first signal on the material or within the material indicates increasing susceptibility of the material to bacterial contamination or colonization. In another preferred embodiment, exposing the material being evaluated to the bacteria comprises using the material as wound closure material in an animal or human. In yet another preferred embodiment, exposing the material being evaluated to the bacteria additionally comprises administering the modified bacteria intravenously to the animal or human.

In a preferred embodiment, the bacteria are modified to produce a second detectable signal, and the method additionally comprises determining whether the second signal is present on the material or within the material. Absence of the second signal on the material or within the material indicates that the material is not susceptible to bacterial contamination or colonization. Presence of the second signal on the material or within the material indicates that the material is susceptible to bacterial contamination or colonization.

FIGURES

The features, aspects and advantages of the present invention will become better understood with regard to the following description, appended claims and accompanying figures where:

DESCRIPTION

Figure 1:
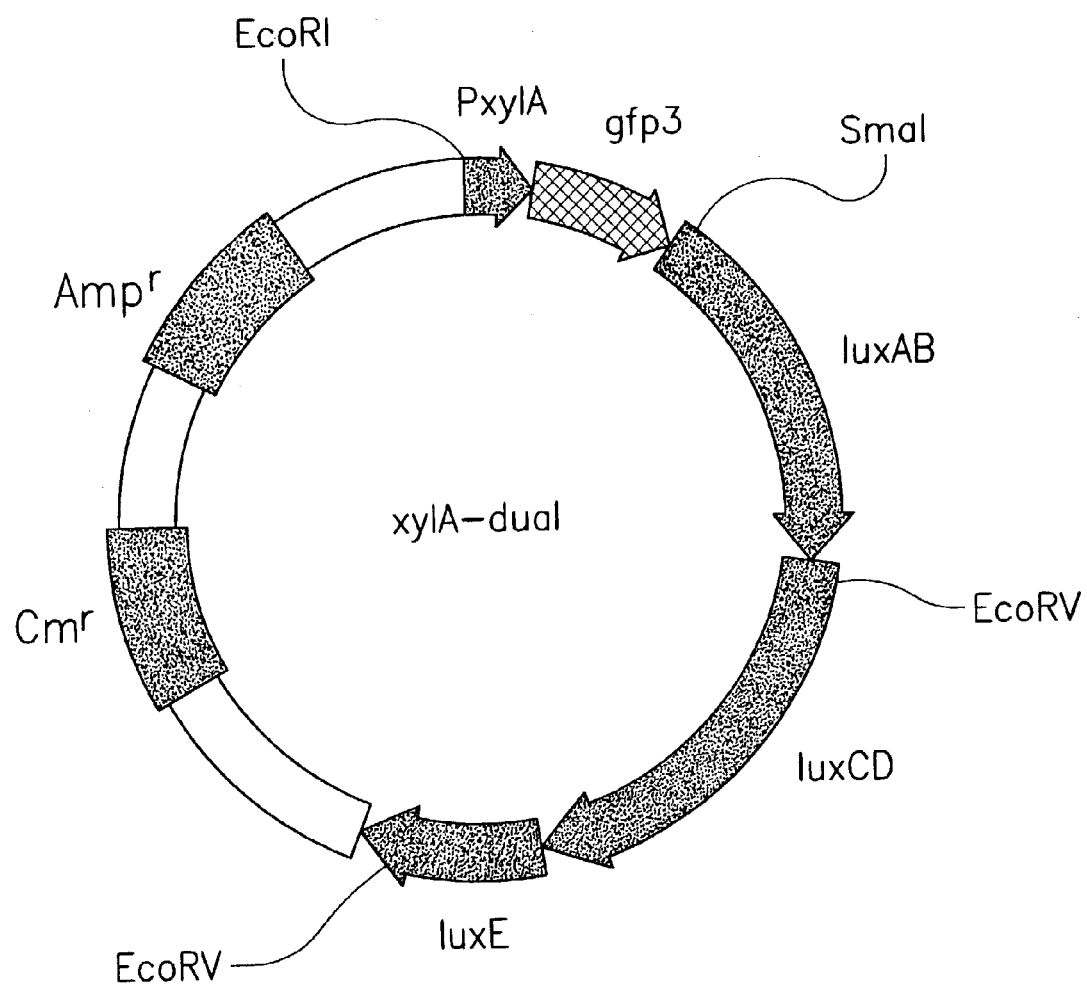
FIG. 1 is a diagram showing the plasmid pXy1A-dual.

The present method allows the testing of materials for implantation to determine whether they can prevent bacteria from passing through or around the material. Additionally, the present method allows the testing of materials for implantation to determine whether they are susceptible to bacterial contamination or colonization. The present method can be used to evaluate dental materials to be used for restorations, endodontic treatment and the surgical repair of teeth, as well as to evaluate wound closure material. However, the present method can also be used to evaluate other materials for implantation into animals or humans, as will be understood by those with skill in the art with reference to this disclosure.

As used in this disclosure, the phrase "passing through or around the material" and equivalent phrases means passing into the material, passing through the material from a first side to a second side and passing between the implanted material and the natural part of the animal or human body at the site of implantation from one side of the material to another. For example, when the implantable material is used as filling material for a tooth cavity, the present method allows the testing of the material to see if bacteria will colonize the material itself on the surface, pass into the material, pass entirely through the filling or pass between the edges of the filling where it forms a seal with the remainder of the natural tooth.

The present method involves the use of modified bacteria. Preferably, the modified bacteria produce a detectable signal when they are living that distinguishes the bacteria from naturally occurring bacteria which might contaminate the apparatuses used in the method. The signal can be any suitable signal as will be understood by those with skill in the art with reference to this disclosure. However, in a preferred embodiment, the signal is light emission in the visible spectrum. In another preferred embodiment, the modified bacteria produce a plurality of such detectable signals when they are living.

In one embodiment, the bacteria are modified to incorporate the cDNA for a functional green fluorescent protein. In another embodiment, the bacteria are modified to incorporate the cDNA for a functional luciferase. In a particularly preferred embodiment, the bacteria are modified to incorporate both the cDNA for a functional green fluorescent protein and the cDNA for a functional luciferase.

One suitable form of cDNA codes for the green fluorescent protein from the jellyfish *Aequorea victoria*. This form of green fluorescent protein emits green light by accepting energy transfer from sources that include exogenous blue light and from some luciferase catalyzed reactions. The UV light stimulated green fluorescent protein fluorescence does not require cofactors and the gene product alone can be sufficient to allow detection of single living cells under the light microscope. However, cDNA's coding for other green fluorescent proteins are also suitable, including modified forms of green fluorescent proteins.

Another suitable form of cDNA codes for a luciferase from *Xenorhabdus luminescens*. However, cDNA's coding for other luciferases are also suitable including modified forms of luciferases.

The method for evaluating whether a material will allow bacteria to pass through or around the material is performed as follows. First, bacteria are provided which have been modified to produce a first detectable signal. The bacteria are placed on a first side of the material being evaluated. Then, the bacteria are left in contact with the material for a period of time ranging from about a few minutes to about several months or more. Next, the presence or absence of the first signal is determined on a second side of the material or within the material. The absence of the first signal on the second side of the material or within the material indicates that the bacteria have not passed through or around the material. The presence of the first signal on the second side of the material or within the material indicates that the bacteria have passed through or around the material.

The method can additionally comprise quantifying the amount of bacteria that will pass through the material by quantifying the amount of the first signal on the second side of the material. Increasing amounts of the first signal on the second side of the material or within the material indicates increasing amounts of bacteria have passed through or around the material.

Further, the bacteria provided can have been modified to produce a second detectable signal. The method can then additionally comprise determining whether the second signal is present on the second side of the material or within the material. The absence of the second signal on the second side of the material or within the material additionally indicates that the bacteria have not passed through or around the material. The presence of the second signal on the second side of the material or within the material additionally indicates that the bacteria have passed through or around the material. The second signal can be used to confirm the results determined by detecting the first signal on the second side. Further, depending on the signals used, the second signal can add specificity to quantification of the amount of bacteria that have passed through or around the material.

In one embodiment, the method comprises placing the modified bacteria in the center of a hollowed out, extracted natural tooth. The root end of the tooth is then sealed with the material. The sealed tooth is placed in a test medium with the sealed end covered by the test medium. After a suitable period of time, a determination is made whether the first signal is present on a second side of the material by detecting the first signal in the test medium. The absence of the first signal on the second side of the material or within the material indicates that the bacteria have not passed through or around the material. The presence of the first signal on the second side of the material or within the material indicates that the bacteria have passed through or around the material. The test medium can be a suitable bacteria culture medium to aid in detection of bacteria that have passed through or around the material by allowing bacterial growth and reproduction.

Similarly, when the bacteria have been modified to produce a second detectable signal, the second signal can also be detected in the test medium when they are living. The absence of the second signal on the second side of the material or within the material indicates that the bacteria have not passed through or around the material. The presence of the second signal on the second side of the material or within the material indicates that the bacteria have passed through or around the material.

In another preferred embodiment, there the modified bacteria are additionally modified to be grown selectively. One suitable type of selective growth is to modify the bacteria to be antibiotic resistant, though other types of selective growth are possible as will be understood by those with skill in the art with reference to this disclosure. When the bacteria have been modified to be antibiotic resistant, a suitable antibiotic can be included on the second side of the material being evaluated to discourage bacterial growth from contamination, rather than from the modified bacteria passing through the material being evaluated.

In a preferred embodiment, the present method is a method to determine whether a material is susceptible to bacterial contamination or colonization. The method comprises providing bacteria which are modified to produce a first detectable signal. Next, the material being evaluated is exposed to the bacteria. Then, a determination is made whether the first signal is present on the material. The absence of the first signal on the material indicates that the material is not susceptible to bacterial contamination or colonization. The presence of the first signal on the material indicates that the material is susceptible to bacterial contamination or colonization.

The method can additionally comprise quantifying the susceptibility of the material to bacterial contamination or colonization by quantifying the amount of the first signal on the material. Increasing amounts of the first signal on the material indicates increasing susceptibility of the material to bacterial contamination or colonization.

In a particularly preferred embodiment, the material being evaluated is used as wound closure material in an animal or human. The material is exposed to the modified bacteria by being placed in the animal or human and then administering the modified bacteria intravenously or by another suitable method to the animal or human. Then, a determination is made whether the first signal is present on the material or within the material.

In another preferred embodiment, the bacteria are modified to produce a second detectable signal. The method additionally comprises determining whether the second signal is present on the material or within the material after exposing the material to the bacteria. The absence of the second signal on the material or within the material indicates that the material is not susceptible to bacterial contamination or colonization. The presence of the second signal on the material or within the material indicates that the material is susceptible to bacterial contamination or colonization.

Examples of the present method will now be described in greater detail. Modified bacteria containing genes to produce a functional green fluorescent protein, a functional luciferase and to contain an antibiotic resistance gene were constructed for use in the method by transformation with a plasmid DNA bearing a cassette with genes producing luciferase, green fluorescent protein and antibiotic resistance as follows. Two constructs were used. The first construct pLITE201 (as disclosed in Voisey C R, Marincs F. Biotechniques, 1998; 24:56) was a plasmid vector with a gram-negative origin of replication containing the lux CDABE cassette from *Xenorhabdus luminescens* driven by the lac promoter. It was purified from DH5α using the Maxi-Prep DNA purification kit (Qiagen GmbH, Santa Clarita, Calif., US). The pLITE201 plasmid was then electroporated into attenuated strains of *Vibrio cholera, Salmonella typhimurium*, and *Shigella* using BioRad® electroporation protocols for the various strains and the BioRad® Gene Pulser II unit (Bio-Rad Laboratories, Hercules, Calif.). Positive transformants were identified by placing the outgrowth plates under the Argus 100 low light imager (Hamamatsu Corp., Hamamatsu, Japan). The positive colonies were confirmed by observing fluorescent bacteria under the fluorescent microscope.

The second construct was a lux ABCDE cassette from pXy1A-dual (Hill, P, University of Nottingham, UK) as shown in FIG. 1, purified using the Maxi-Prep kit (Qiagen). This plasmid has a gram-positive origin of replication as well as gram-positive ribosomal binding sites, which allowed expression in gram-positive organisms. The plasmid was then transformed into *Enterococcus faecalis* (strains JH2-2, ATCC4082, and OG1X) using electroporation with the BioRad® Gene Pulser II (Bio-Rad Laboratories, Hercules, Calif.).

Transformation was accomplished as follows. First, a pre-culture of the *E. faecalis* strains was used to inoculate 15 ml of BYGT broth containing 0.7% glycine to weaken the cell walls. The concentration of glycine was determined as that necessary to reduce bacterial growth as determined by the optical density at 600 or 600 nm by about 70% to 90%. Next, the overnight culture was diluted into pre-warmed BYGT broth containing 0.7% glycine to bring the OD(600) to 0.06–0.08 and the cells were incubated in 37° C. without agitation for 1 hour. Then, the cells were chilled on ice and harvested by centrifugation.

Next, the cells were washed twice with electroporation buffer (0.625 M sucrose, 1 mM $MgCl_2$, pH 4) and the cells were aliquoted into 100:1 volumes and incubated on ice for 30 minutes or deep frozen for later use. Approximately 300 ng of DNA was added and the cells were electroporated using 0.2 cm cuvettes, field strength 6,250 V/cm, resistance 200 Ω, and 25 $\mu$F capacitance. The cells were placed on ice for about 1–2 minutes and were diluted into 1 ml THB medium plus antibiotics (Chloramphenicol) and then, incubated at 37° C. for 90–120 minutes. Next, the cells were plated on THB agar with 0.25 M sucrose and antibiotics. Colonies were observed in 48 hours under the low light imager (Hamamatsu) and the presence of the plasmid was confirmed by observation of fluorescent bacteria under the fluorescent microscope.

The method of testing materials for implantation to determine whether they can prevent bacteria from passing through the material according to the present invention was performed as follows. Extracted natural teeth were placed in bleach for 24 hours to remove the organic debris from the external surfaces. Some of the material being tested was tested as dental restorations placed in the coronal aspect of the teeth. Preparations for these tests were made according to the standard protocols for amalgam, composite and crown restorations. The preparations were filled by the test material. Each tooth was placed in a container having a suitable growth medium, antibiotic and the modified bacteria and left for about 48 hours. Then the teeth were removed, sectioned and examined to determine if the bacteria penetrated the material. Luminescence was confirmed by examination under a low light imager.

The second application tested was as root repair material. The root canal system was cleaned out to leave a hollow center space in the teeth. The root-end was resected 3 mm from the apex with a high speed, hand drill and a fissure burr, and the root-end was prepared to receive a retrofitting material with a high speed, hand drill and a #2 round burr. The test material was used to seal the root end.

Figure 2:
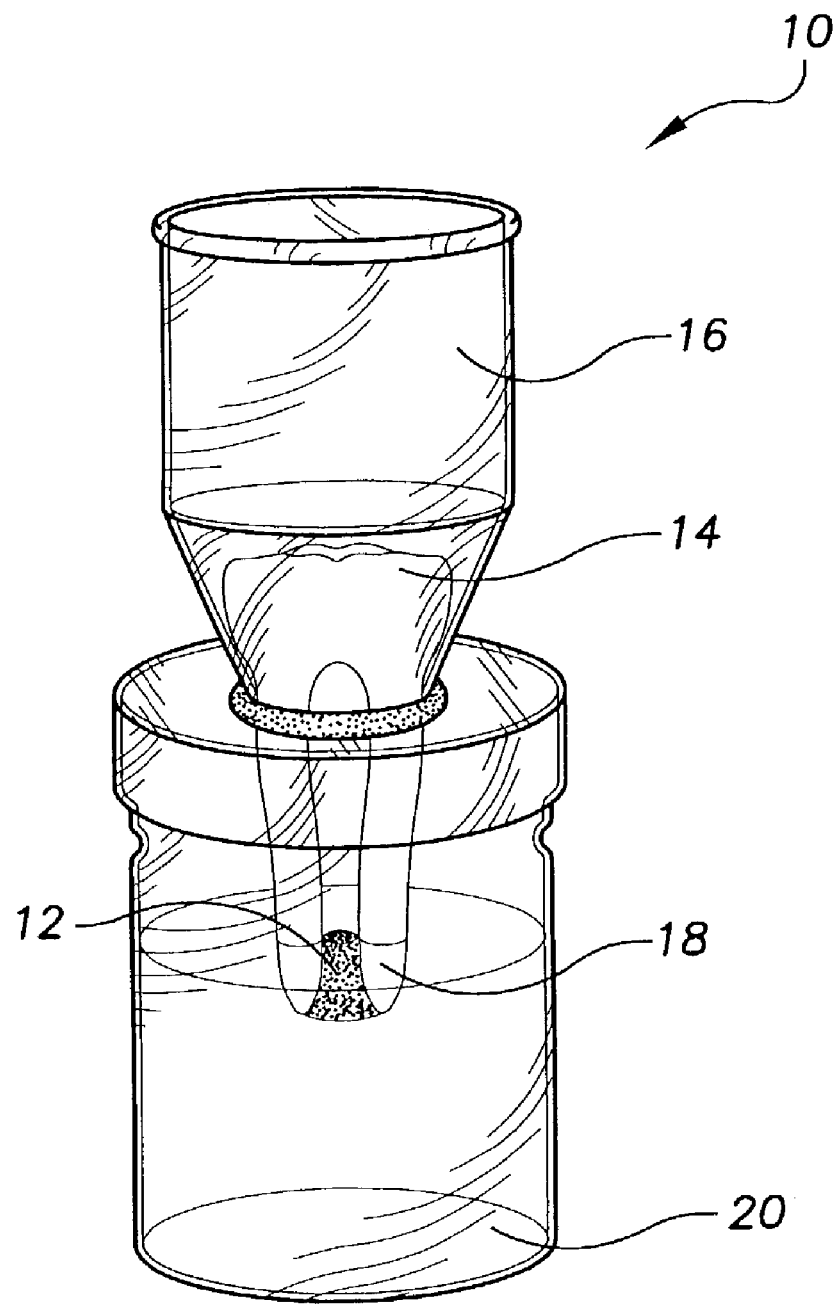
FIG. 2 is a diagram of an apparatus used for testing materials to determine whether the material will allow bacteria to pass through according to the present invention.

Referring now to FIG. 2, there is shown a diagram of an apparatus 10 used for testing materials 12 to determine whether the material will allow bacteria to pass through according to the present invention. Each tooth 14, prepared as described above, was fitted into a microcentrifuge tube 16 and sealed into place using sticky wax so that the root apex 18 was protruding from the tube 16 and fit onto a lower compartment 20 of an apparatus 10. The lower compartment 20 contained liquid broth media and antibiotic or contained solid media and antibiotic, and each tooth was placed into the media. The media and antibiotic were selected based on the strain and antibiotic resistance gene being used. The lid of the microcentrifuge tube was then opened and each tooth 14 was filled with the labeled bacteria in the same liquid broth media containing the antibiotic.

Leakage of bacteria into the media in the lower chamber 20 was evaluated by placing the media in the chamber under a low light imager, or in a luminometer if liquid media was used, (not shown) to measure the presence or absence of labeled bacteria. Leakage was found when using some materials indicating that the material did not prevent passage of bacteria. Therefore, this method can be used to determine whether a material can prevent bacteria from passing through the material.

The method of testing materials for implantation to determine whether they are susceptible to bacterial contamination or colonization according to the present invention was performed as follows. First, an incision was made in the animal skin and the incision was closed by the material being tested in the form of sutures. Approximately $10^7$ modified bacterial were intravenously injected into the animal through the femoral vein or through the tail vein. The animals were monitored daily to determine if the modified bacteria were present on the material being tested as indicated by the presence of luminescence at the incision wound under the low light imager. For some materials, no luminescence was present on the material. For other materials, varying amounts of luminescence was present. Therefore, this method can be used to predict whether a material is susceptible to bacterial contamination or colonization when implanted into an animal or human.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for an evaluation of an implantable material to determine whether the implantable material is susceptible to bacterial contamination or colonization when implanted into a living animal or human comprising:
   a) providing bacteria which are modified to produce a first detectable signal;
   b) exposing the implantable material being evaluated to the modified bacteria by intravenously introducing the modified bacteria into a living animal or human; and
   c) determining by in vivo detection whether the first signal is present on the implantable material or within the implantable material;
   where absence of the first signal on the implantable material or within the implantable material indicates that the implantable material is not susceptible to bacterial contamination or colonization and where presence of the first signal on the implantable material or within the implantable material indicates that the implantable material is susceptible to bacterial contamination or colonization; and where the implantable material is non-living.

2. The method of claim 1, additionally comprising quantifying the susceptibility of the implantable material to bacterial contamination or colonization by quantifying the amount of the first signal on the implantable material or within the implantable material;
   where increasing amounts of the first signal on the implantable material or within the implantable material indicates increasing susceptibility of the implantable material to bacterial contamination or colonization.

3. The method of claim 2, where exposing the implantable material being evaluated to the modified bacteria comprises using the implantable material as wound closure material in an animal or human.

4. The method of claim 3, where exposing the implantable material being evaluated to the modified bacteria additionally comprises administering the modified bacteria intravenously to the animal or human.

5. The method of claim 1, where the bacteria are modified to produce a second detectable signal, and where the method additionally comprises determining whether the second signal is present on the implantable material or within the implantable material;
   where absence of the second signal on the implantable material or within the implantable material indicates that the implantable material is not susceptible to bacterial contamination or colonization and where presence of the second signal on the implantable material or within the implantable material indicates that the implantable material is susceptible to bacterial contamination or colonization.

6. The method of claim 1, where the first signal is light emission in the visible spectrum.

7. The method of claim 5, where the second signal is light emission in the visible spectrum.

8. The method of claim 1, where the bacteria are modified to incorporate a functional green fluorescent protein.

9. The method of claim 1, where the bacteria are modified to incorporate a functional luciferase.

10. The method of claim 1, where the bacteria are modified to incorporate both a functional green fluorescent protein and a functional luciferase.

* * * * *